US010755809B2

(12) United States Patent
Kehoe et al.

(10) Patent No.: US 10,755,809 B2
(45) Date of Patent: Aug. 25, 2020

(54) HOME MEDICATION MANAGER

(71) Applicants: The Research Foundation for The State University of New York, Albany, NY (US); Tim Kehoe, Smithtown, NY (US); Rob Barnikel, Fort Salonga, NY (US)

(72) Inventors: Tim Kehoe, Smithtown, NY (US); Rob Barnikel, Fort Salonga, NY (US); Craig Lehmann, Aquebogue, NY (US); John Brittelli, Brookhaven, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 16/317,088

(22) PCT Filed: Jul. 13, 2017

(86) PCT No.: PCT/US2017/041824
§ 371 (c)(1),
(2) Date: Jan. 11, 2019

(87) PCT Pub. No.: WO2018/013746
PCT Pub. Date: Jan. 18, 2018

(65) Prior Publication Data
US 2019/0295704 A1    Sep. 26, 2019

Related U.S. Application Data

(60) Provisional application No. 62/361,761, filed on Jul. 13, 2016.

(51) Int. Cl.
*G08B 1/00*      (2006.01)
*G16H 20/13*    (2018.01)
(Continued)

(52) U.S. Cl.
CPC ............... *G16H 20/13* (2018.01); *A61J 7/04* (2013.01); *G06Q 50/22* (2013.01); *G09B 5/02* (2013.01); *G16H 20/10* (2018.01); *G16H 40/67* (2018.01)

(58) Field of Classification Search
CPC ...................................................... G16H 6/00
(Continued)

(56) References Cited

U.S. PATENT DOCUMENTS 7,844,361 B2 *  11/2010  Jean-Pierre ......... G06F 19/3462
                                                                700/236
2003/0086338 A1 *  5/2003  Sastry ................. G06F 19/3462
                                                                368/10
(Continued)

FOREIGN PATENT DOCUMENTS

WO    WO 2006/084310 A1    8/2006
WO    WO 2014/199374 A1   12/2014

OTHER PUBLICATIONS

International Search Report dated Sep. 11, 2017 issued in PCT/US2017/041824.

*Primary Examiner* — Tai T Nguyen
(74) *Attorney, Agent, or Firm* — Scully, Scott, Murphy & Presser, P.C.

(57) ABSTRACT

A home medication management system and method are provided comprise a home medication management device, a computing device associated with a user of medication management system, and a server in communication with the home medication management device and the computing device. The server comprises memory storing an application program interface (API) that is configured to manage the home medication of a patient including the registration of prescriptions, transmission of the registered prescriptions to the home medication management device, association of medications of the registered prescriptions with recesses of (Continued)

the home medication management device, presentation of alerts to the patient at scheduled times to take the medications based on the prescriptions, monitoring the patient for compliance with the alerts, determining whether the patient has taken the medication as scheduled, and presenting the determination to the user via the computing device.

15 Claims, 14 Drawing Sheets

(51) Int. Cl.
*A61J 7/04* (2006.01)
*G16H 20/10* (2018.01)
*G09B 5/02* (2006.01)
*G06Q 50/22* (2018.01)
*G16H 40/67* (2018.01)

(58) Field of Classification Search
USPC .......... 340/309.7, 309.16, 573.1, 666, 691.1, 340/691.7; 368/1, 10
See application file for complete search history.

(56) References Cited

U.S. PATENT DOCUMENTS

| | | |
|---|---|---|
| 2007/0016443 A1* | 1/2007 | Wachnnan .......... G06F 19/3456 705/2 |
| 2012/0189177 A1* | 7/2012 | Oh ........................ G06K 9/228 382/128 |
| 2013/0123977 A1 | 5/2013 | Sanders et al. |
| 2014/0350720 A1 | 11/2014 | Lehmann et al. |
| 2015/0072231 A1* | 3/2015 | Kudoh .................. H01M 2/263 429/209 |
| 2015/0100335 A1* | 4/2015 | Englehard .......... G06F 19/3462 705/2 |

* cited by examiner

HOME MEDICATION MANAGER

CROSS-REFERENCE TO RELATED APPLICATIONS

This application claims the benefit of U.S. Provisional Application No. 62/361,761 filed on Jul. 13, 2016, the entire contents of which are incorporated herein by reference.

FIELD OF THE INVENTION

The present disclosure relates generally to medication management, and in particular to medication management in a home setting without the need for an on-site caregiver.

BACKGROUND

Often it is difficult for a patient to remember to take prescribed medication. This can be especially true for patients who are prescribed multiple medications that need to be taken at different frequencies and times of day. This problem can be compounded by patient confusion, reduced short-term memory, etc. Missing a dose of medication, accidently taking a pill twice, and/or adverse interaction between prescribed medications are all significant causes of adult visits to emergency rooms. For example, according to data reported by Medicare, heart failure patients were prescribed an average of twelve (12) medications, and some were prescribed as many as thirty (30) different types of medication. With half of these medications taken 2 or 3 times per day, this amounts to over 100 pills per day, all needing to be coordinated to be taken at specific times and following specific instructions, such as taken with meals, with water, while fasting, etc. In the year 2000, the costs of medication-related morbidity in ambulatory care setting exceeded $177.4 billion. Moreover, lack of medication compliance after discharge from the hospital is a primary reason for patients being re-admitted.

Because of these issues and others, it is imperative that today's technology provide appropriate clear directions on when a particular medication is needed and how it is to be taken (e.g. with food and/or water). Hence there is a need for portable home medication reminders, medication dispensers and devices that combine informing and dispensing functions that can help patients manage their medications and reduce the risk that a patient will miss taking his medication in the home or while traveling. Moreover, home medication management systems that provide guidance and maintain the integrity of the original packaging will limit the potential for a user to take a prescribed medication inadvertently, which may increase the possibility of adverse effects caused by such a medication.

SUMMARY OF THE DISCLOSURE

In an aspect of the present disclosure a home medication management system is disclosed. The home medication management system comprises a home medication management device of a patient comprising a recess that is configured to store a medication container, a computing device associated with a user of medication management system, and a server in communication with the home medication management device and the computing device. The server comprises at least one processor comprising hardware and memory storing an application program interface (API) that is configured to manage the home medication of a patient. The API, when executed by the at least one processor, is configured to prompt the user via the computing device to register a prescription for a patient registered to an account of the user and receive from the user, via the computing device, prescription information about a medication included in the prescription. The prescription information may comprise a name of the medication, a dosage of the medication, a frequency at which the patient needs to take the medication, and a date and time that the patient will start taking the medication. The API may be further configured to register the prescription for the patient based on the received prescription information, and transmit the registered prescription to the home medication management device of the patient. The home medication management device may be configured to associate the medication of the registered prescription with the recess of the home medication management device, provide an indication of the associated recess to the patient for the reception of a medicine container containing the medication, determine that the medication container containing the medication has been received within the associated recess, present an alert to the patient at a scheduled time to take the medication based on the prescription information, and provide an indication of the associated recess to the patient. The indication may identify the recess as containing the medication container for the medication that the patient is scheduled to take. The home medication management device may be further configured to monitor the patient for compliance with the alert by determining whether the medication container containing the medication has been removed from the associated recess and transmit compliance data based on the monitoring to the server. The API may be further configured to receive the compliance data from the home medication management device, determine, based on the received compliance data, whether the patient has taken the medication as scheduled, and present the determination to the user via the computing device.

In some aspects, the determination of whether the patient has taken the medication as scheduled may include determining whether a pre-determine amount of time has elapsed since the alert was presented to the patient without the patient taking the medication. In yet further aspects, the determination may be presented to the user only if the predetermined amount of time has elapsed.

In another aspect, the user may be the patient.

In yet another aspect, the user may be selected from the group consisting of a doctor of the patient, a caregiver of the patient, an emergency contact of the patient, and a relative of the patient.

In an aspect, the presentation of the determination to the user may comprise at least one of a text message, an e-mail, and a push notification.

In some aspects, the API may be configured to present to the user via the user device at least one report comprising at least one of medication lists for the patient, historical data on the patient's compliance with scheduled medications, and data on emergency notifications.

In another aspect, the API may be further configured to present to the patient via a computing device associated with the patient at least one of clinical history of the patient, prescription history of the patient, compliance history of the patient, current prescriptions registered to the patient in the API, and future prescriptions registered to the patient in the API.

In yet another aspect, the compliance history may comprise a percentage of medications that the patient has taken as scheduled in a period of time.

In some aspects, the API may be further configured to prompt the user via the computing device to set access rights for users associated with the patient and receive from the user via the computing device access right settings for users associated with the patient.

In an aspect of the present disclosure a home medication management method is disclosed. The method comprises prompting, by an application program interface (API) executed by at least one hardware processor of a server, a user, via a computing device, in communication with the server to register a prescription for a patient registered to an account of the user and receiving, by the API, from the user, via the computing device, prescription information about a medication included in the prescription. The prescription information comprises a name of the medication, a dosage of the medication a frequency at which the patient needs to take the medication, and a date and time that the patient will start taking the medication. The method further comprises registering, by the API, the prescription for the patient based on the received prescription information, transmitting, by the API, the registered prescription to a home medication management device of the patient that is in communication with the server, associating, by the home medication management device, the medication of the registered prescription with a recess of the home medication management device, providing, by the home medication management device, an indication of the associated recess to the patient for the reception of a medicine container containing the medication, determining, by the home medication management device, that the medication container containing the medication has been received within the associated recess, presenting, by the home medication management device, an alert to the patient at a scheduled time to take the medication based on the prescription information, providing, by the home medication management device, an indication of the associated recess to the patient, the indication identifying the recess as containing the medication container for the medication that the patient is scheduled to take, monitoring, by the home medication management device, the patient for compliance with the alert by determining whether the medication container containing the medication has been removed from the associated recess, transmitting, by the home medication management device, compliance data based on the monitoring to the server, receiving, by the API, the compliance data from the home medication management device, determining, by the API, based on the received compliance data, whether the patient has taken the medication as scheduled; and presenting, by the API, the determination to the user via the computing device.

In some aspects, the determination of whether the patient has taken the medication as scheduled may include determining whether a pre-determine amount of time has elapsed since the alert was presented to the patient without the patient taking the medication. In an aspect, the determination may be presented to the user only if the predetermined amount of time has elapsed.

In an aspect the user may be the patient.

In yet other aspects, the user may be selected from the group consisting of a doctor of the patient, a caregiver of the patient, an emergency contact of the patient, and a relative of the patient.

In an aspect, the presentation of the determination to the user may comprise at least one of a text message, an e-mail, and a push notification.

In some aspects, the method may further comprise presenting, by the API, to the user via the user device at least one report comprising at least one of medication lists for the patient, historical data on the patient's compliance with scheduled medications, and data on emergency notifications.

In another aspect, the method may further comprise presenting, by the API, to the patient via a computing device associated with the patient at least one of, clinical history of the patient, prescription history of the patient, compliance history of the patient, current prescriptions registered to the patient in the API, and future prescriptions registered to the patient in the API.

In some aspects, the compliance history may comprise a percentage of medications that the patient has taken as scheduled in a period of time.

In yet another aspect, the method may further comprise prompting, by the API, the user via the computing device to set access rights for users associated with the patient, and receiving, by the API, from the user via the computing device access right settings for users associated with the patient.

A computer readable storage medium storing a program of instructions executable by a machine to perform one or more methods described herein also is also provided.

BRIEF DESCRIPTION OF THE DRAWINGS

These and other features, aspects, and advantages of the present invention will become better understood with regard to the following description, appended claims, and accompanying drawings wherein:

DETAILED DESCRIPTION

Figure 1:
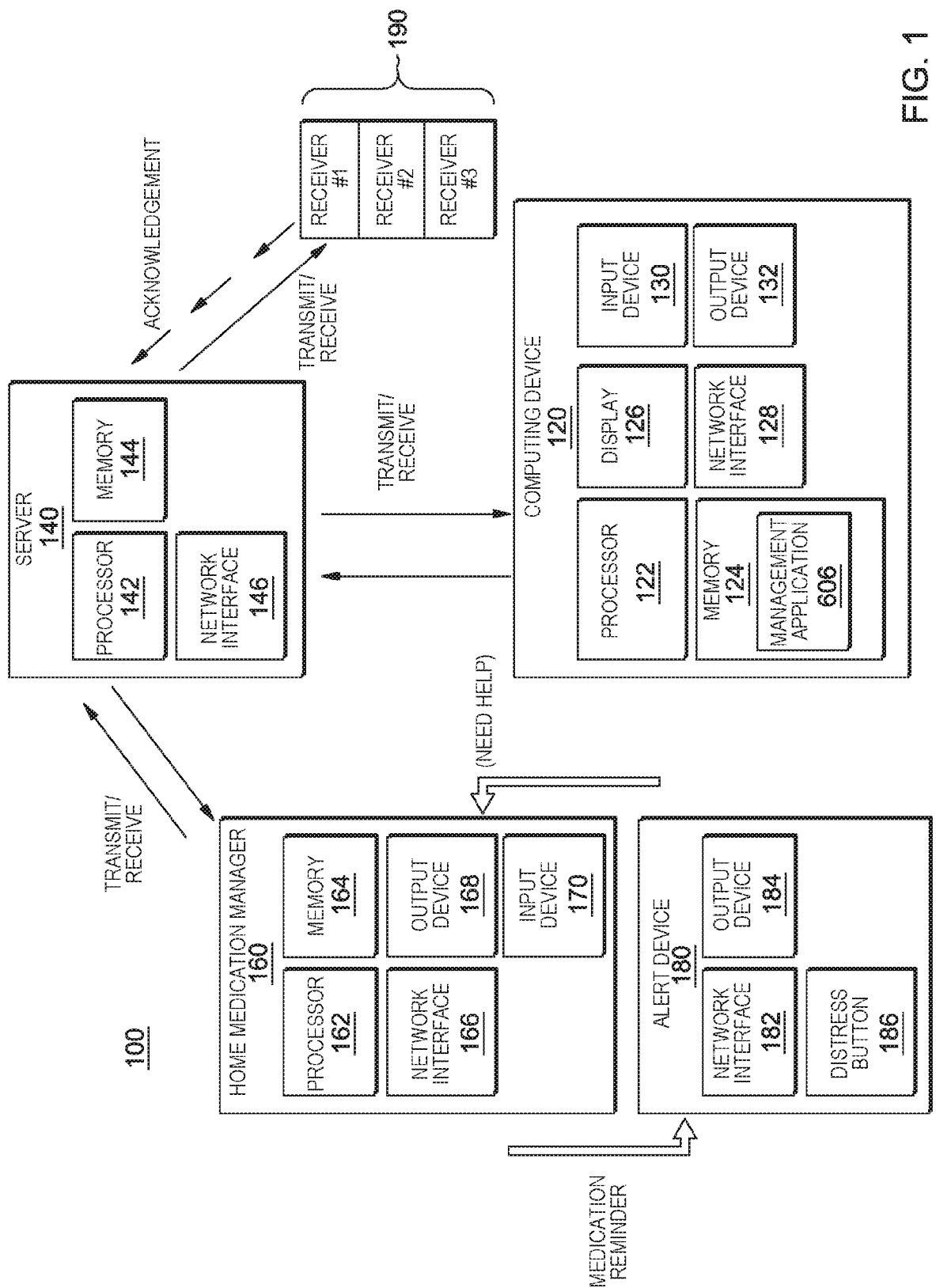
FIG. 1 is a system diagram of a medication management system in accordance with an aspect of the present disclosure.
Figure 2:
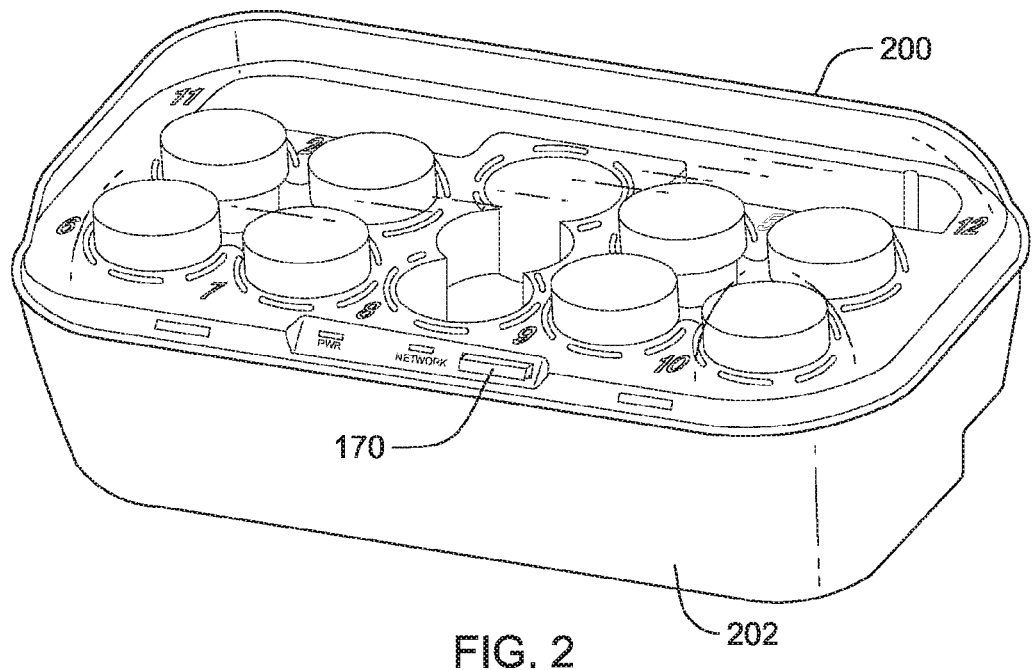
FIG. 2 is a three dimensional representation of the front of a home medication manager in accordance with an aspect of the present disclosure.
Figure 3:
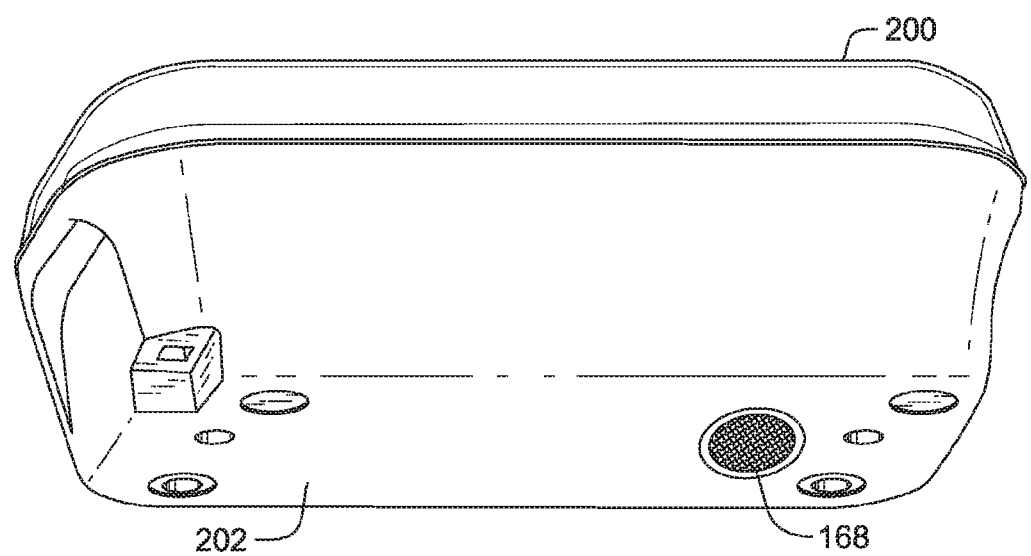
FIG. 3 is a three dimensional representation of the rear of the home medication manager of FIG. 2 in accordance with an aspect of the present disclosure.
Figure 4:
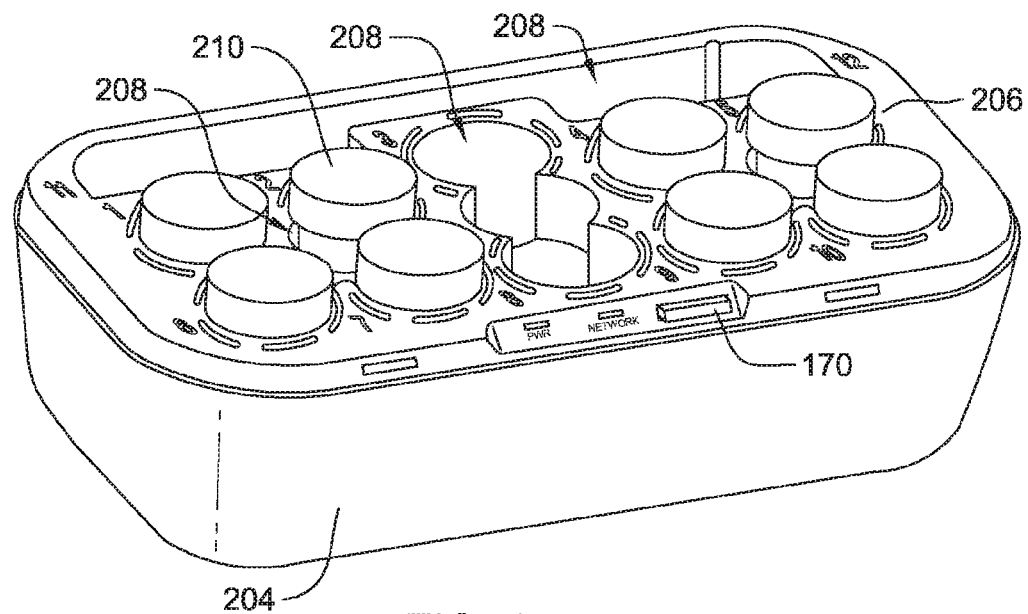
FIG. 4 is a three dimensional representation of the home medication manager of FIG. 2, with a lid removed in accordance with an aspect of the present disclosure.
Figure 5:
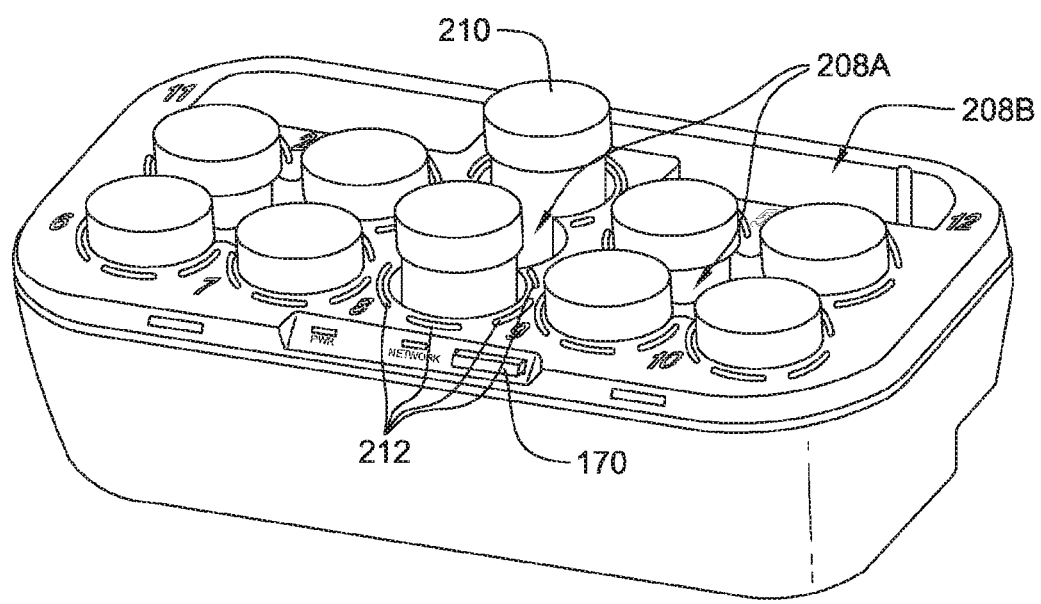
FIG. 5 is an illustration of medication containers inserted into recesses of the home medication manager of FIG. 4 in accordance with an aspect of the present disclosure.

FIG. 1 illustrates an embodiment of the present disclosure in which a home medication management system 100 comprises a computing device 120, a server 140, a home medication manager 160, an alert device 180, and a plurality of receivers 190.

Computing device 120 may include, for example, at least one processor 122, memory 124, a display 126, a network interface 128, an input device 130, output device 132, and any other feature common to a computing device. Computing device 120 may include, for example, personal computers, tablets, laptops, smart phones, smart watches, smart wearable devices, handheld devices, mobile devices, or other computing devices that may be accessed or used by a user.

Processor 122 may include, for example, a microcontroller, Field Programmable Gate Array (FPGA), or any other processor that is configured to perform various operations. Processor 122 may be configured to execute instructions as described below. These instructions may be stored, for example, in memory 124.

Memory 124 may include, for example, non-transitory computer readable media in the form of volatile memory, such as random access memory (RAM) and/or cache memory or others. Memory 124 may include, for example, other removable/non-removable, volatile/non-volatile storage media. By way of non-limiting examples only, memory 124 may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Display 126 may include, for example, a computer monitor, television, smart television, a display screen integrated into a personal computing device such as, for example, laptops, smart phones, smart watches, virtual reality headsets, smart wearable devices, or any other mechanism for displaying information to a user. In some aspects, display 126 may include a liquid crystal display (LCD), an e-paper/e-ink display, an organic LED (OLED) display, or other similar display technologies. In some aspects, display 126 may be touch-sensitive and may also function as an input device 130.

Network interface 128 is configured to transmit and receive data or information to and from computing device 120 via wired or wireless connections. For example, network interface 128 may utilize wireless technologies and communication protocols such as Bluetooth®, WIFI (e.g., 802.11a/b/g/n), cellular networks (e.g., CDMA, GSM, M2M, and 3G/4G/4G LTE), near-field communications systems, satellite communications, or any other form of communication that allows computing device 120 to transmit or receive information. Network interface 128 may allow computing device 12 to communicate directly with one or more of server 140, home medication manager 160, alert device 180, and receivers 190. In some aspects network interface 128 may communicate with via an intermediary network, for example, a local area network (LAN), wide area network (WAN), the internet, or other similar networks. Network interface 128 may be configured to provide encryption and decryption when sending or receiving personal health-related information in order to maintain patient privacy. In some aspects, the data will be HIPAA (Health Insurance Portability and Accountability Act) compatible.

Input device 130 may include, for example, a keyboard, a mouse, a touch-sensitive display, a keypad, a microphone, or any other input devices that may be used alone or together to provide a user with the capability to interact with computing device 110.

Output device 132 may include, for example, speakers, vibration mechanisms, display 126, an illumination component such as, for example, a light emitting diode, or other similar output devices that provide information to a user. For example, output device 132 may present a graphic user interface to a user, e.g., via display 126, may present information audibly via a speaker, may provide an alert, indication, or other information via a vibration mechanism such as, for example, an electric motor or other similar vibrations mechanisms commonly found in mobile devices.

Server 140 may include at least one processor 142, memory 144, a network interface 146, and any other feature commonly found in a server. In some aspects, server 140 may be a web server. Memory 144 and network interface 146 may be similar to memory 124 and network interface 128 of computing device 120. In some aspects, server may be configured to wired or wirelessly communicate with computing device 120, for example, via network interfaces 128 and 146.

With reference now to FIGS. 1-5, home medication manager 160 may include at least one processor 162, memory 164, a network interface 166, an output device 168, and an input device 170. Memory 164 and network interface 166 may be similar to memory 124 and network interface 128 of computing device 120. In some aspects, home medication manager 160 may be configured to wired or wirelessly communicate with computing device 120, server 140, or both, for example, via network interfaces 128 and 146, and 166. Output device 168 may be or include any of the output devices 132 described above for computing device 120.

Input device 170 may be or include any of the input devices 130 described above for computing device 120. In some aspects, input device 170 may include a button or other actuatable element that may be activated by a user.

In some aspects, for example, input device 170 may be activated to update or change a function of the home medication manager 160. For example, input device 170 may be activated by a user to update the home medication manager 160, e.g., recalculating what medications have been received within home medication manager 160. For example, input device 170 may be depressed or actuated for a predetermined period of time, e.g., 3 seconds or less, to activate updating of the home medication manager 160. Any other pre-determined period of time may be used. When input device 170 is activated to update home medication manager 160, home medication manager 160 may communicate with a patient account on server 140 or with API 602 to determine whether any changes to medication or scheduling are present and may update the settings of home medication manager 160 based on any changes found on the patient's account or API 602. In some aspects, for example, the patient may wish to activate input device 170 to update the home medication manager 160 when the patient initially sets up home medication manager 160 or when the patient adds new, additional, or replacement medications to home medication manager 160.

In some aspects, updating of the home medication manager 160 may also or alternatively occur automatically without requiring activation of input device 170. For example, updating may occur periodically, e.g., hourly, daily, weekly, monthly, etc., or at a pre-determined time during each day, e.g., at 4:00 A.M or any other time. Any periodic or pre-determined time may be used for automatically updating home medication manager 160. Automatic updating may be useful in the case where the patient forgets to activate input device 170 to update home medication manager 160 after making a change to the medication.

In some aspects, for example, input device 170 may be activated by a user to place the home medication manager 160 in a sleep mode. For example, input device 170 may be depressed or actuated for a predetermined period of time, e.g., 4-7 seconds, to activate sleep mode. Any other pre-determined period of time may be used. In some aspects, for example, if the user is traveling and home medication manager 160 will be placed in luggage, the user may wish to set the home medication manager 160 to sleep mode so that it will not make noise or issue alerts during travel. When in sleep mode, some or all of the functions of home medication manager 160 may be shut down or inactive. For example, battery power may be interrupted or inhibited from supplying power to one or more of the functions of home medication manager 160.

In some aspects, for example, input device 170 may also be activated to wake the home medication manager 160 up after sleep mode, i.e., to resume normal operation. For example, input device 170 may be depressed or actuated for a predetermined period of time, e.g., 8-10 seconds, to wake up the home medication manager 160 from sleep mode. Any other pre-determined period of time may be used. When home medication manager 160 wakes up, home medication manager 160 may return to the functional state prior to being placed into sleep mode.

In some aspects, the user may also or alternatively cycle through the update, sleep mode, and wake functions of home medication manager 160 by activating input device 170 multiple times. For example, each activation of input device 170 may cause home medication manager 160 to issue an audible indication of the action, e.g., update, sleep mode, wake, etc., to be taken by home medication manager 160 in response to activation of the input device 170, e.g., via output device 168. Once the user hears the appropriate audible indication, the user may stop activating input device 170 and the function may be executed after a pre-determined period of time, e.g., 5 seconds. Any other pre-determined period of time may be used.

With reference now to FIGS. 2-5, home medication manager 160 includes lid 200 and a base housing 202. In some aspects, lid 200 may be separable from base housing 202 and may be removably securable to based housing 202, for example, via a snap-fit connection, a lock-fit connection, or other similar methods of removable securement to base housing 202. In some aspects, lid 200 may be affixed or attached to base housing 202, for example, via a joint, hinge or other similar method of affixing or attaching that allows a user at least partially open or remove lid 200 for access to base housing 202.

Base housing 202 includes an outer shell 204 and top surface 206. Top surface 206 may be formed separately from outer shell 204 or may be integrally formed with outer shell 204. For example, in some aspects, top surface 206 may be configure for insertion into a cavity (not shown) of base housing 204 and may be secured or affixed to base housing 204, for example, via snap-fit, lock-fit, adhesives, or other similar methods of affixing the top surface 206 to base housing 204.

Top surface 206 may include a plurality of recesses 208 that may be configured to receive medication containers 210. In some aspects, recesses 208 may have a variety of sizes and shapes in order to accommodate various sizes and shapes of medication containers 210. For example, one or more recesses 208A may be configured to receive a variety of medication containers 210 including, for example, 6 dram, 8 dram, 13 dram, 16 dram, 20 dram, 30 dram 40 dram, 60 dram, or any other size of medication container 210. In some aspects, one or more of recesses 208B may be configured to receive medication provided in an alternative form of packaging such as, for example, blister packs. In some aspects, medication containers 210 may be the same containers that a user of home medication management system 100 receives from a doctor or pharmacists when a prescription is filled thereby preserving the original labeling including the name of the medication, dosage, frequency, warning labels, and ordering physician name. For example, medication containers 210 may the intact, unaltered, or original medication container received from a doctor or pharmacy. Medication containers 210 may be containers that are configured to hold, for example, pills, fluid, or other types of medication.

In some aspects, medication containers 210 may be removably secured within recesses 208. For example, medication containers 210 secured within recesses 208 by a friction fit, tension (e.g., through the use of springs (not shown) or spring like materials), snap-fit, locking clasps, magnets, or other similar mechanisms for removably securing medication containers 210 within recesses 208. In some aspects, lid 200, when secured to body housing 202 may secure or otherwise inhibit medication containers 210 from being removed or otherwise escaping recesses 208.

In some aspects, top surface 206 may include one or more illumination elements 212 positioned around one or more of recesses 208. In some aspects, one or more of illumination elements 212 may be configured to light up or illuminate to provide an indication to a user of a recess 208 in which to place a particular medication container 210. In some aspects, one or more of illumination elements 212 may be configured to light up or illuminate to provide an indication to the user of which recess 208 contains a medication container 210 storing a particular medication that the user is scheduled to take. For example, one or more illumination elements 212 may be positioned near or adjacent to a particular recess 208 containing a medication container 210 storing a medication that the user is scheduled to take and may be illuminated to indicate to the user that the medication container 210 is located within that particular recess 208.

Illumination elements 212 may include, for example, light emitting diodes (LEDs), fluorescent, compact fluorescent lamps (CFLs), incandescent, fiber optic, or other similar forms of lighting. In some aspects, a plurality of illumination elements 212 may be positioned radially around one or more of recess 208. For example, a particular recess 208 may include one, two, three, four, or more illumination elements 212 positioned radially around the particular recess 208 and configured to light up or illuminate to draw a user's attention to the particular recess 208.

In some aspects, illumination elements 212 may be illuminated when the user removes the wrong medication container 210 from one of recesses 208. For example, if a first of the recesses 208 contains a medication container 210 for a medication that the user is scheduled to take, and the user instead removes a medication container 210 from a second of the recesses 208, home medication manager 160 may illuminate one or more of illumination elements 212 to indicate that the wrong medication has been taken. For example, illumination elements 212 adjacent to or near the first recess 208 may illuminate in a first color, for example, green, yellow, etc., to indicate the medication container 210 that the user is supposed to remove while illumination elements 212 adjacent to or near the second recess 208 may illuminate in another color, e.g., red, when the user removes the medication container 210 from the second recess 208 to indicate that the wrong medication has been removed.

In some aspects, each recess 208 may include a detector that is configured to detect when a medication container 210 is inserted into the recess. In some aspects, the detector may be, for example, a photo detector, a pressure sensor, a switch, or other similar devices for detecting the presence of a medication container 210 within a recess 208.

In some aspects, base housing 202 may include output device 168, for example, a speaker, display, etc., which can be used to provide a user with audio and/or visual prompts and/or notifications. For example, if a user removes the wrong medication container 210 from a recess 208, output device 168 may present a warning to the user in audio form, visual form, or both. In some aspects, output device 168 may audibly, visually, or both, indicate the medication that the user is scheduled to take in conjunction with illumination elements 212.

In some aspects, home medication manager 160 may be powered by an AC power source (not shown). In some aspects, may also or alternatively be powered by a rechargeable or non-rechargeable battery (not shown). In some aspects, the battery may be a Lithium-Ion battery.

Referring again to FIG. 1, alert device 180 may include, for example, a wired or wireless device that is configured to alert a user that it is time to take a medication or to transmit distress alerts to computing devices 120 associated with emergency contacts or emergency services in event that the patient is in distress. In some aspects, alert device 180 may include a network interface 182, an output device 184, and an alert button 186. In some aspects network interface 182 and output device 184 may be similar to those found in computing device 120. For example, output device 184 may be configured to provide an audio indication, a visual indication, or both, to a user indicating that it is time to take a medication. Distress button 186 may be activated by the patient to indicate that the patient is in distress. Activation of distress button 186 may cause a distress alert to be transmitted via network interface 182 to one or more of home medication manager 160, server 140, computing devices 120 associated with the patient's emergency contacts, computing devices 120 associated with emergency services, computing devices associated with the patient's doctors or caregivers, and receivers 190 associated with any of the emergency contacts, emergency services, doctors, and caregivers. In some aspects, a computing device 120 of the patient may also or alternatively perform the functions of alert device 180. In some aspects, alert device 180 may be a standalone device and may additionally include some or all of the features of computing device 120.

In some aspects, alert device 180 may be a wearable device such as, for example, a bracelet, watch, necklace, pendent, earpiece, pin, or any other device that may be worn or affixed to the user. In some aspects alert device may be a smart device, for example, a smart watch, smart phone, smart bracelet, etc. In some aspects, alert device 180 may be configured to output an alert to a patient, for example, via output device 184 indicating that the patient should take a medication. Alert device 180 may be configured to receive a signal from one or more of computing device 120, server 140, and home medication manager 160, for example, via one or more of network interfaces 132, 146, 166, and 184, and to present or provide an indication via output device 184 to the patient that a medication needs to be taken. In some aspects, the user may access or activate distress button 186 of alert device 180 to transmit a message to one or more computing devices 120, server 140, home medication manager 160, and receivers 190, for example, via one or more of network interfaces 132, 146, 166, and 184 indicating that the user requires further assistance or is in distress.

Receivers 190 may be communication devices associated with users, doctors, caregivers, emergency services, or any other party that may be associated with the care of the patient. Receivers 190 may include some or all of the features of computing device 120.

Figure 6:
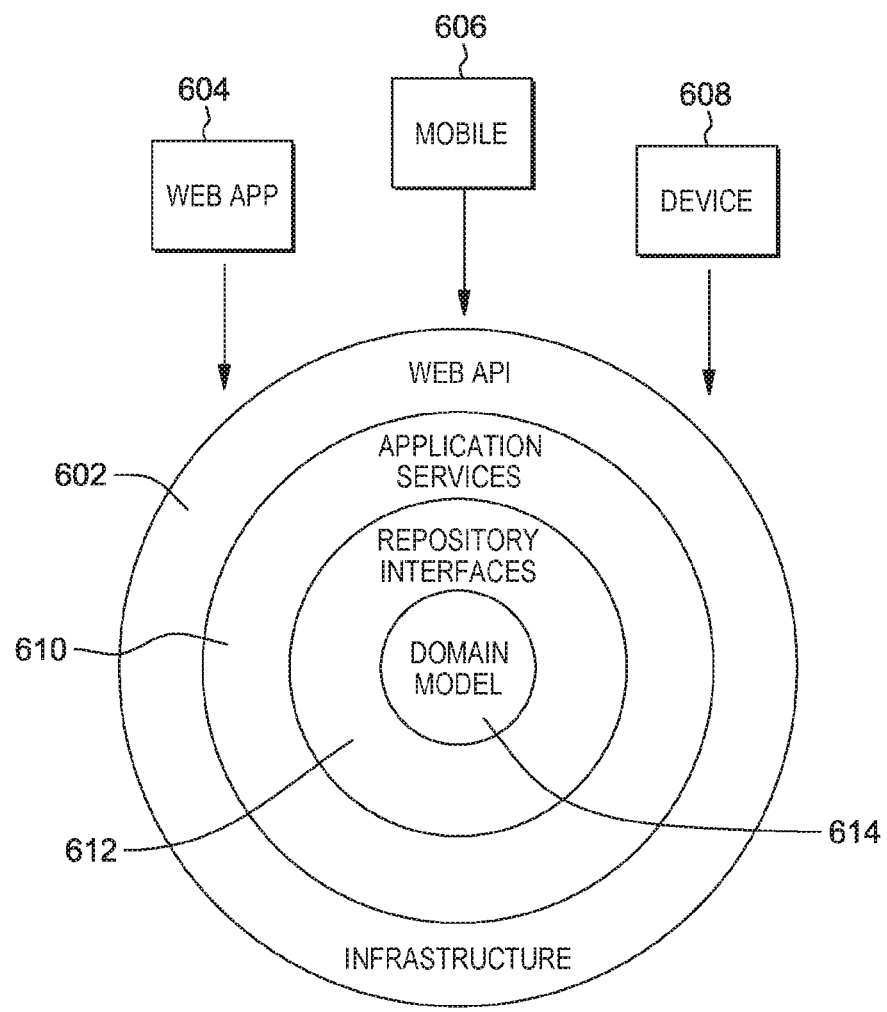
FIG. 6 is a diagram of a system architecture of the medication management system of claim 1 in accordance with an aspect of the present disclosure.

Referring now to FIG. 6, server 140 may include an application program interface (API) 602 for managing home medication manager 160. API 602 may be stored in memory 144 and may be executable by processor 142. In some aspects, API 602 may be configured to communicate with computing device, for example, via network interfaces 128 and 146. In some aspects, API 602 may be accessible by computing device 120 via a web application or web page interface 604. For example, computing device 120 may open or access the web page interface 604 using a common web browser. In some aspects, an application 606 associated with API 602 may be installed on computing device 602 and may be configured to transmit and receive information to and from API 602. For example, application 606 may be an application installed on a mobile device. Web page interface 604 and application 606 may provide a user of computing device 120 with a graphical user interface with which to interact with API 602. In some aspects, application 606 may download information and other data associated with medication management to the computing device 120. In some aspects, application 606 may store the downloaded information and other data in memory 124.

In some aspects, API 602 may be configured to communicate with home medication manager 160, for example, via network interfaces 146 and 166. For example, API 602 may transmit an indication to home medication manager 160 that it is time for a user to take medication from a medication container 210 that is currently stored in a recess 208 of home medication manager 160. API 602 may instruct home medication manager 160 to illuminate illumination elements 212 adjacent to or around the recess 208 storing the medication. API 602 may also instruct home medication manager 160 to transmit an alert to alert device 180. The alert may be presented to the user by alert device 180, for example, via a visual indication, audio indication, or vibration. In some aspects, the alert may cause the alert device 180 to indicate that it is time to take a medication without specifying which medication is to be taken. In some aspects, the alert may cause the alert device 180 to also or alternatively present the user with the specific medication that is to be taken. In some aspects, API 602 may be configured to communicate directly with alert device 180, for example, via network interfaces 146 and 182 and to transmit the alert directly to alert device.

API 602 includes applications services 610, repository interfaces 612, and a domain model 614.

Figure 7:
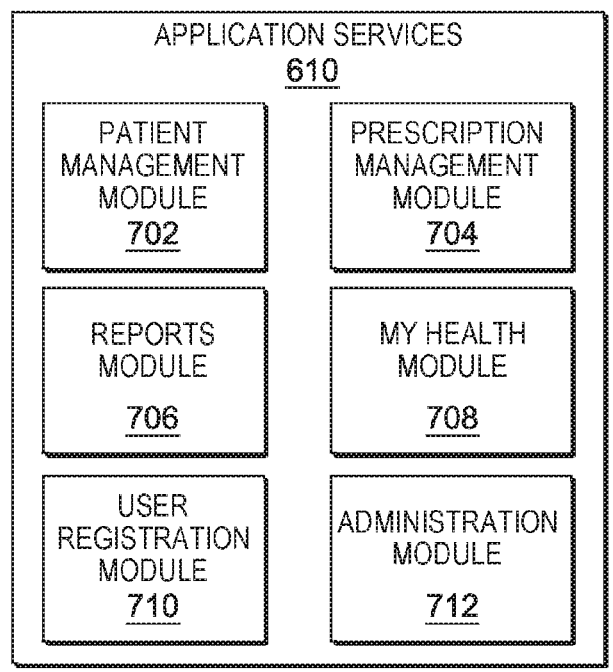
FIG. 7 is a schematic example of the application services of the system architecture of FIG. 6 in accordance with an aspect of the present disclosure.
Figure 8:
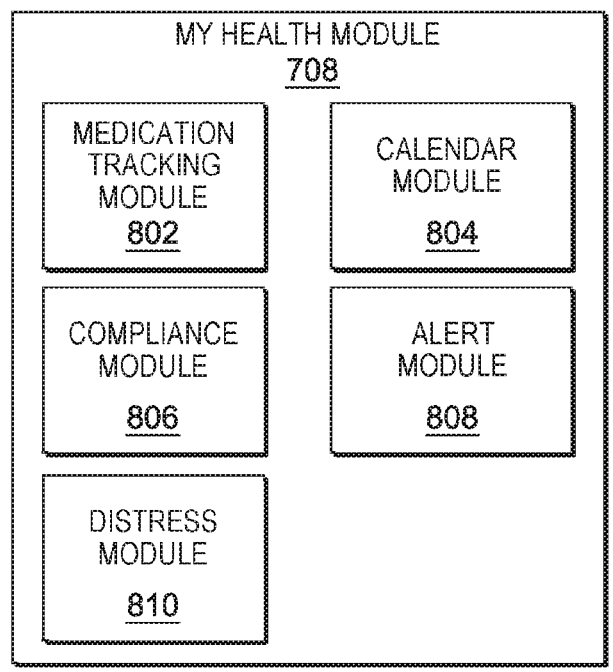
FIG. 8 is a schematic example of the My Health module of the application services of FIG. 7 in accordance with an aspect of the present disclosure.

With reference now to FIG. 7, application services 610 include software modules that implement medication management for a patient. Application services 610 may include, for example, a patient management module 702, prescription management module 704, reports module 706, my health module 708, user registration module 710, and an administration module 712.

Patient management module 702 provides a user with tools to manage patient information including general information, physician information, pharmacy information, emergency contact information, allergies, and current health conditions. For example, the user may input the information via computing device, the information may be retrieved directly from the prescription, e.g., by scanning a barcode, visually imaging the prescription and performing image processing, or other similar data extraction methods, the information may be retrieved from a medical database, or other similar sources. In some aspects, the user may be the patient. In some aspects, the user may be a doctor, caregiver, relative, or other party associated with the patient.

Prescription management module 704 provides a user with tools to manage prescription information and scheduling. For example, the user may add prescriptions to a patient account and may schedule the dispensing of prescriptions on the patient account, which may each include one or more medications. When a prescription is registered, the user may choose a frequency, quantity, and duration of the prescription. The user may also select one or more reminders for the prescription from a number of pre-defined options. As a non-limiting example, selectable reminders may include audible alerts, e-mails, text messages to a phone or computer, buzzers, visible reminders, vibration (tactile) reminders, reminders provided via computing device 120, reminders via home medication manager 160, reminders via alert device 180, or other similar reminders. In some aspects, the reminders may be transmitted to one or more of computing device 120, home medication manager 160, and alert device 180. For example, the reminders may be sent to the patient via SMS, e-mail, push notifications, or other forms of notification on one or more of computing device 120, home medication manager 160, and alert device 180. In some aspects, the reminders may also be transmitted to computing devices 120 of other users of system 100 that are associated with the patient, for example, doctors, caregivers, relatives, etc.

In some aspects, the registered prescriptions may be transmitted to the home medication manager 160 and stored in memory 164 of home medication manager 160. In some aspects, the user may modify or suspend a prescription using prescription management module 704 and the modification or suspension may be transmitted to home medication manager 160 for storage in memory 164.

In some aspects, if a medication has not been taken by the patient as scheduled, a reminder may be sent to the patient. For example, the reminder may be transmitted a computing device 120 of the patient, to home medication manager 160, or to alert device 180. In some aspects, the reminder may be transmitted after a predetermined period of time has elapsed since the scheduled time. For example, the reminder may be transmitted if ninety minutes have passed since the patient was supposed to take the medication. In some aspects, the pre-determined amount of time may be specified by the user when the user adds, modifies, or suspends the prescription using prescription management module 704. In some aspects, the reminder may also or alternatively be provided to other users of system 100 associated with the patient, e.g., doctors, caregivers, relatives, etc. In some aspects, the user may be the patient. In some aspects, the user may be a doctor, caregiver, relative, or other party associated with the patient.

Reports module 706 presents a user of system 100 with a variety of reports. For example, the reports may be presented via a user interface associated with API 602, e.g., via web interface 604 or application 606. In some aspects, reports module 706 may generate reports including, for example, lists of medications that the patient is current scheduled to take, lists of medications that the patient was previously scheduled take, lists of medications that the patient has completed, lists of medications for the patient that have been suspended, etc. In some aspects, reports module 706 may generate a report providing a user with historical data on patient compliance with scheduled medications. The report may include, for example, a compliance rate (percentage, units, or other similar measures), missed or delayed medication, or other compliance related data over a unit of time (e.g., by day, week, month, quarter, half-year, year) or by medicine. In some aspects, reports module 706 may generate reports including data on emergency notifications including, for example, how many emergency notifications have been issued, when the emergency notifications were issued, the medication for which the emergency notification was issued, etc. In some aspects, the user may be the patient. In some aspects, the user may be a doctor, caregiver, relative, or other party associated with the patient.

My Health module 708 is specifically tailored for exclusive use of the patient as a user. My Health module 708 provides the patient with access to his or her clinical history, prescription history, current prescriptions, and any future prescriptions that may have been entered into the system. For example, the patient may access My Health module 708 via a user interface associated with API 602. My health module 708 includes sub-modules that perform various functions for the patient including a medication tracking module 802, calendar module 804, compliance module 806, alerts module 808, and distress button 810.

Medication tracking module 802 is configured to track and store medication history of the patient, for example, whether a medication was taken as scheduled, rescheduled, or suspended. The medication history may be stored, for example, in memory 144 via repository interface 612.

Calendar module 804 provides the patient with an overview of his or her medication schedules. For example, calendar module 804 may provide the patient with detailed schedules for when each medication should be taken by minute, hour, day, etc. In some aspects, calendar module 804 may also indicate time periods under which the patient should not take specific medications, for example, when taking two medications at the same time may cause a problem.

Compliance module 806 provides the patient with an overview of his or her compliance to the medication schedules including, for example, a percentage of compliance and units of compliance. In some aspects, the compliance may be presented to the patient by day, week, or any other unit of time. In some aspects, the patient's compliance may be presented to the patient separately for each medicine.

Alerts module 808 is configured to transmit alerts to the patient in the even that the patent missed taking a scheduled medication or took the wrong medication. Alerts module 808 may transmit the alert to the patient's computing device 120, e.g., via SMS, email, push notifications, or other similar systems. In some aspects, alerts module 808 may allow the patient to set custom alerts. For example, the patient may upload or record custom alerts depending on the patient's particular needs, medications, etc. In some aspects, the custom alerts may be an additional layer of alerts. For example, where a default alert is a text message, the patient may also set a custom alert set an additional custom alert to be a phone call.

Distress module 810 is configured to transmit a distress alert to users or contacts other than the patient. For example, if the patient is in distress, the patient may activate a distress button 186 on alert device 180. Distress button 186 may transmit a distress alert signal to home medication manager 160 which may then transmit a distress alert signal to server 140. Server 140 may then transmit an alert signal to computing device 120 or receivers 190 associated with any users identified as emergency contacts for the patient, to computing devices 120 associated with emergency services, to computing devices 120 associated with the patient's doctors or caregivers, or to computing devices 120 associated with any other party that is involved in caring for the patient and receiving distress alerts. In some aspects, alert device 180 may transmit the distress alert signal directly to server 140, directly to the associated computing devices 120, or directly to receivers 190 without requiring home medication manager 160 or server 140 to forward the alert signal to the associated computing devices 120 or receivers 190.

Referring again to FIG. 7, user registration module 710 is configured to guide a new user through a registration process with API 602. For example, the new user may be required to input an identifier associated with a home medication manager 160 that has been registered by an administrator of system 100. Once the identifier has been provided, the user may create an account that is linked to the home medication manager 160 associated with the identifier and utilize modules 702, 704, 706 and 708 (if the user is the patient).

Figure 9:
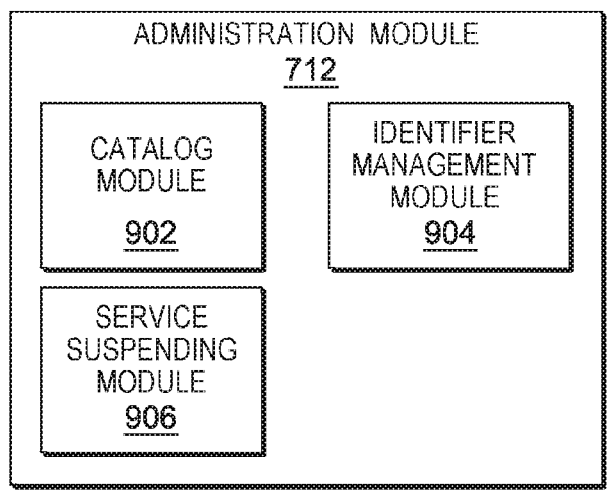
FIG. 9 is a schematic example of the administration module of the application services of FIG. 7 in accordance with an aspect of the present disclosure.

With reference now to FIGS. 7 and 9, administration module 712 is configured to provide an administrator of system 100 with a catalog module 902, an identifier management module 904 for managing home medication managers 160, and service suspending module 906.

Catalog module 902 provides an administrator of system 100 with tools to manage catalogs related to, for example, medicines, dosages, physician types, or other similar prescription related information. In some aspects, the catalogs may be pre-loaded with information, for example, common dosage amounts for particular medications, common medications and dosages prescribed by particular physician types, etc.

Identifier management module 904 provides an administrator of system 100 with the tools to manage home medication managers 160. For example, identifier management module 904 may receive requests from a user to associate a user account with a home medication manager 160 having a particular identifier. Identifier management module 904 may compare the requested identifier with a list of identifiers for home medication managers 160 that have been sold or are known to be active in the marketplace to determine if the request is valid. In some aspects, identifier management module 904 may also be used to identify and replace a damaged home medication manager 160. For example, where a home medication manager 160 has been damaged and replaced, identifier management module 904 may automatically change the association of user accounts from the identifier of the damaged home medication manager 160 to the identifier of a replacement home medication manager 160.

Service suspending module 906 provides the administrator with the capability to suspend or activate access to a specific user account. For example, service suspending module 906 may receive as an input an identifier associated with a home medication manager 160 and may suspend or activate one or more of the user accounts associated with the received identifier.

In some aspects, access rights for individual users or groups of users may be set by a user or administrator of system 100. For example, a user may log into the system and set access rights for patients, users, or other individuals associated with a patient. In some aspects, for example, the user may be the patient. For example, the patient may restrict or enable other users, e.g., on an individual or group basis, from viewing, registering, or modifying prescriptions, medications, custom alerts, from receiving alert data, or other similar features. In some aspects, a user of system that has an account associated with a patient may set access rights for the patient and other user accounts associated with the patient. Non-limiting examples of individuals or groups that may have their access rights restricted or set by the user include, licensed caregivers (e.g., licensed nurse), family members, the patient, pharmacists, physicians, physician assistants (e.g., nurse, nurse practitioner, aide, etc.), or other similar groups that may have or require access to system 100.

Figure 10:
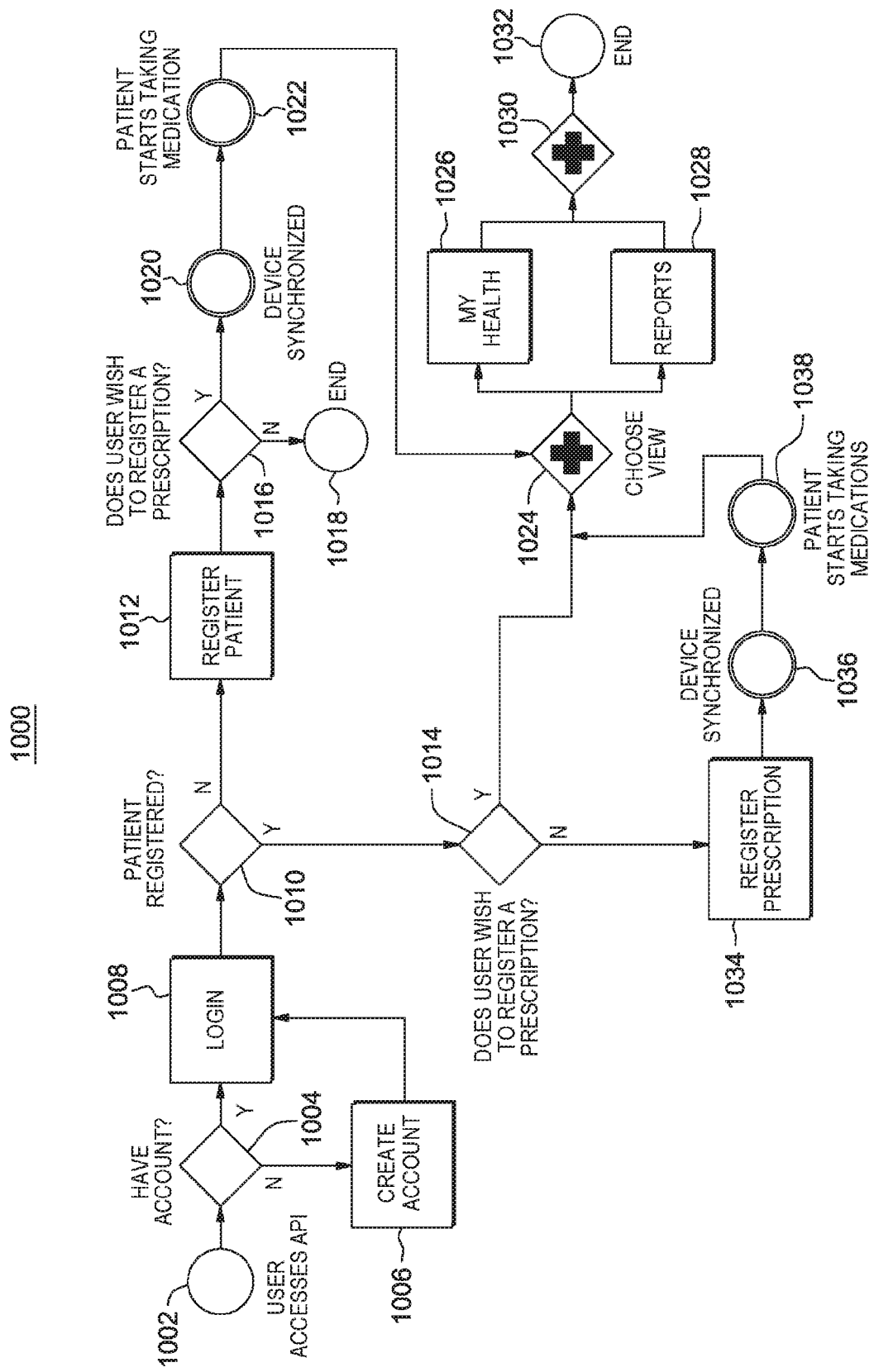
FIG. 10 is a flow diagram illustrating a system flow of the application program interface (API) of the system architecture of FIG. 6 in accordance with an aspect of the present disclosure.

Referring now to FIG. 10, a system flow diagram 1000 is illustrated. At 1002, a user accesses API 602, for example, via web interface 604 or application 606. At 1004, API 602 queries the user to determine whether the user already has an account. For example, with reference to FIG. 11A, API 602 may present a user interface 1100 via web interface 604 or application 606 including elements that are activatable by the user to indicate whether the user already has an account. For example, user interface 1100 may include a username field 1102, a password field 1104, a login element 1106 and a create account element 1108. The user may activate create account element 1108 to indicate that a new account needs to be created and may proceed to 1006 to create a new account as described in more detail below with reference to FIG. 13. The user may alternatively enter a user name and password in fields 1102 and 1104 and activate the login element 1106 to log in at 1008. In some aspects, the user may be separately presented with fields 1102 and 1104 upon activation of login element 1106. Once the user has created an account at 1006, the user may login at 1008, for example, by entering a user name and password in user interface 1100 and activating login element 1106.

At 1010, API 602 determines whether a patient has been registered. For example, if the user account is a newly created account, no patient may be registered to the user account and a patient may be registered at 1012 as described in more detail below with reference to FIG. 14. If the user account was an existing account and the user logged in at 1008, a patient may or may not be registered to the account. If no patient is registered to the existing account, the user may register the patient at 1012. If a patient is already registered with the existing account, API 602 may present the user with the option to select the registered patient by proceeding to 1014 or to register a new patient at 1012. In some aspects, for example, a user accessing API 602 may have more than one patient registered to their account. For example, in the case where the user is a doctor or caregiver, the user may manage prescriptions for a number of different patients. In this case, API 602 may present the user with a list of patients that are registered to the user's account. The user may then select a particular patient from the list at 1010 and proceed to 1014.

At 1016, API 602 determines whether the user wishes to register a prescription for the patient. For example, API 602 may present an element in a user interface via web interface 604 or application 606 that may be activatable by the user to register a prescription for the patient. API 602 may also present an element in a user interface via web interface 604 or application 606 that may be activatable by a user to indicate that the user does not wish to register a prescription for the patient at this time. If the user does not wish to register a prescription, the flow proceeds to 1018 and ends. If the user activates the element to register a prescription, the user may register a prescription as described below with reference to FIG. 15 and then proceed to 1020.

At 1020, API 602 may synchronize the registered prescription and patient information with home medication manager 160. For example, API 602 may transmit the registered prescription and patient information from server 140 to home medication manager 160 via network interfaces 146 and 166. Home medication manager 160 may store the received prescription and patient information in memory 164 for use in providing scheduling reminders and alerts to the patient.

At 1022, the patient may be scheduled to start taking the medication according to the registered patient and prescription information transmitted to home medication manager 160.

Figure 11A:
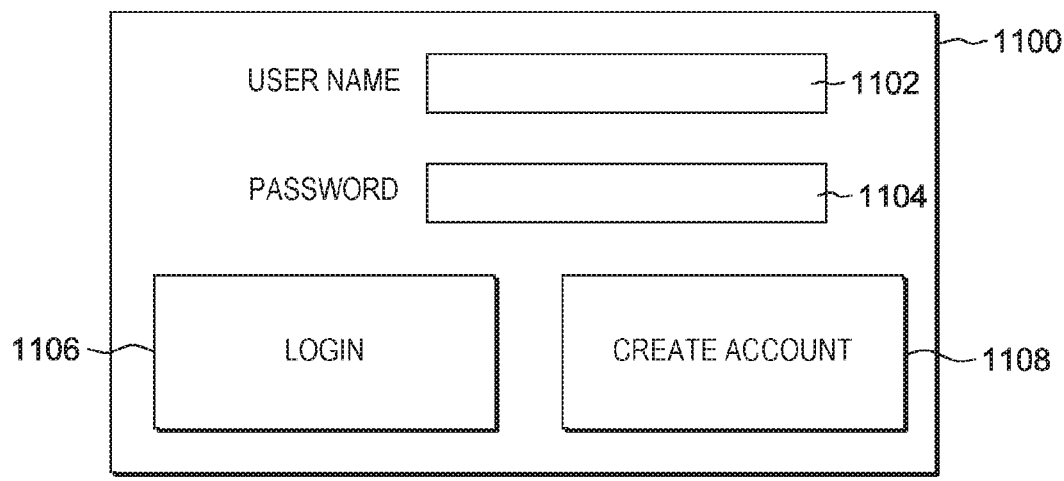
FIG. 11A-11C are illustrations of an example user interfaces that may be presented by the API of FIG. 10 in accordance with an aspect of the present disclosure.
Figure 11B:
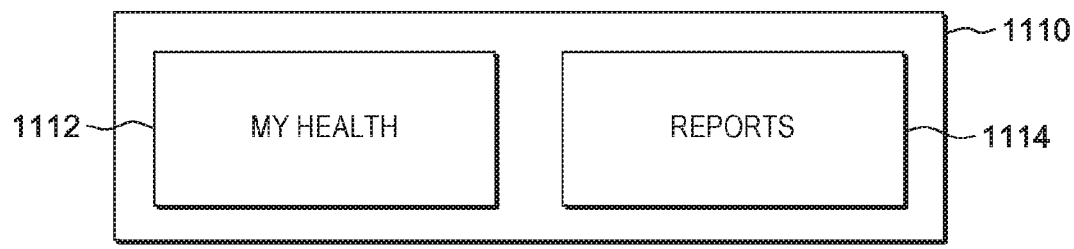

Once the patient and prescriptions have been registered and the patient has been scheduled to start taking the medication, the user proceeds to 1024. With reference now to FIG. 11B, at 1024, API 602 presents the user with a user interface 1110 including an element 1112 that is activatable by the user to provide the user with access the My Health module 708 and an element 1204 that is activatable by the user to provide the user with access to reports module 706. In some aspects, element 1202 may only be available for selection by a user who is the patient. If the user activates element 1112, My Health module 708 may be presented to the user at 1026. If the user activates element 1114, reports module 706 may be presented to the user at 1028.

After the user has reviewed my health module 708 or reports module 706, the flow proceeds to 1028 where the user may be provided user interface 1110 to the user again to allow the user to further select my health module 708 or reports module 706. When the user has finished reviewing my health module 708 and reports module 706, the flow may end at 1032.

Figure 11C:
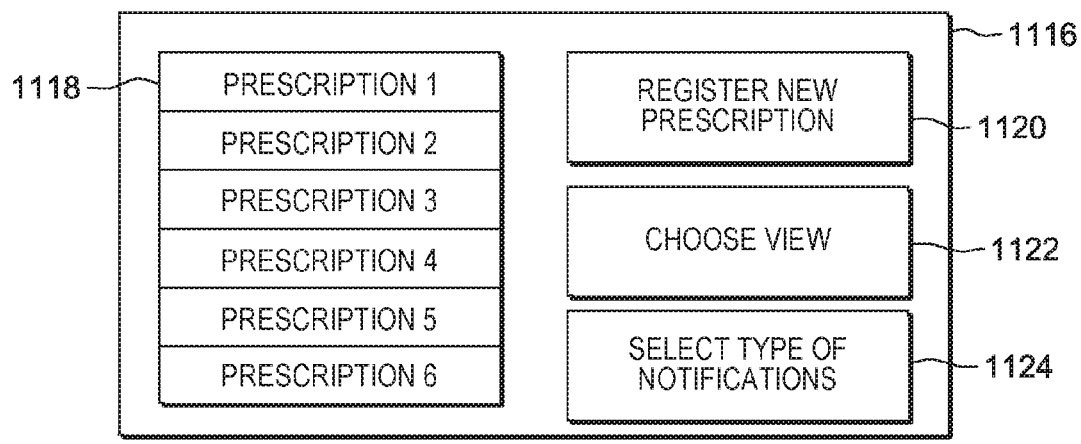

Referring again to 1010, if the patient is already registered, the flow proceeds to 1014. At 1014, API 602 may determine whether any prescriptions are registered to the patient and may present a list of the registered prescriptions to the user in a user interface 1116 via web interface 604 or application 606 as shown, for example, in FIG. 11C. In some aspects, an element 1118 of the user interface 1116 may be associated with each prescription and may be activatable by the user to present additional information about the prescription. API 602 may also present to the user an element 1120 that is activatable to register a new prescription for the patient. In some aspects, API 602 may also present to the user may also an element 1122 that is activatable to proceed to 1024 and choose to view my health module 708 or reports module 706 as described above. In some aspects, API 602 may also present to the user an element 1124 that is activatable to select the type of notifications that the user wishes to receive, e.g., SMS, e-mail, push notifications, visual indications, audio indications, etc.

When the user activates element 1120 to add a new prescription for the patient, the flow proceeds to 1034 where the user may register the new prescription as described below with reference to FIG. 15 and the flow may proceed to 1036.

At 1036, API 602 may synchronize the registered prescription and patient information with home medication manager 160. For example, API 602 may transmit the registered prescription and patient information from server 140 to home medication manager 160 via network interfaces 146 and 166. Home medication manager 160 may store the received prescription and patient information in memory 164 for use in providing scheduling reminders and alerts to the patient.

At 1038, the patient may be scheduled to start taking the medication according to the registered patient and prescription information transmitted to home medication manager 160.

Once the prescription has been registered and the patient has been scheduled to start taking the medication, the user proceeds to 1024 as described above.

Figure 12:
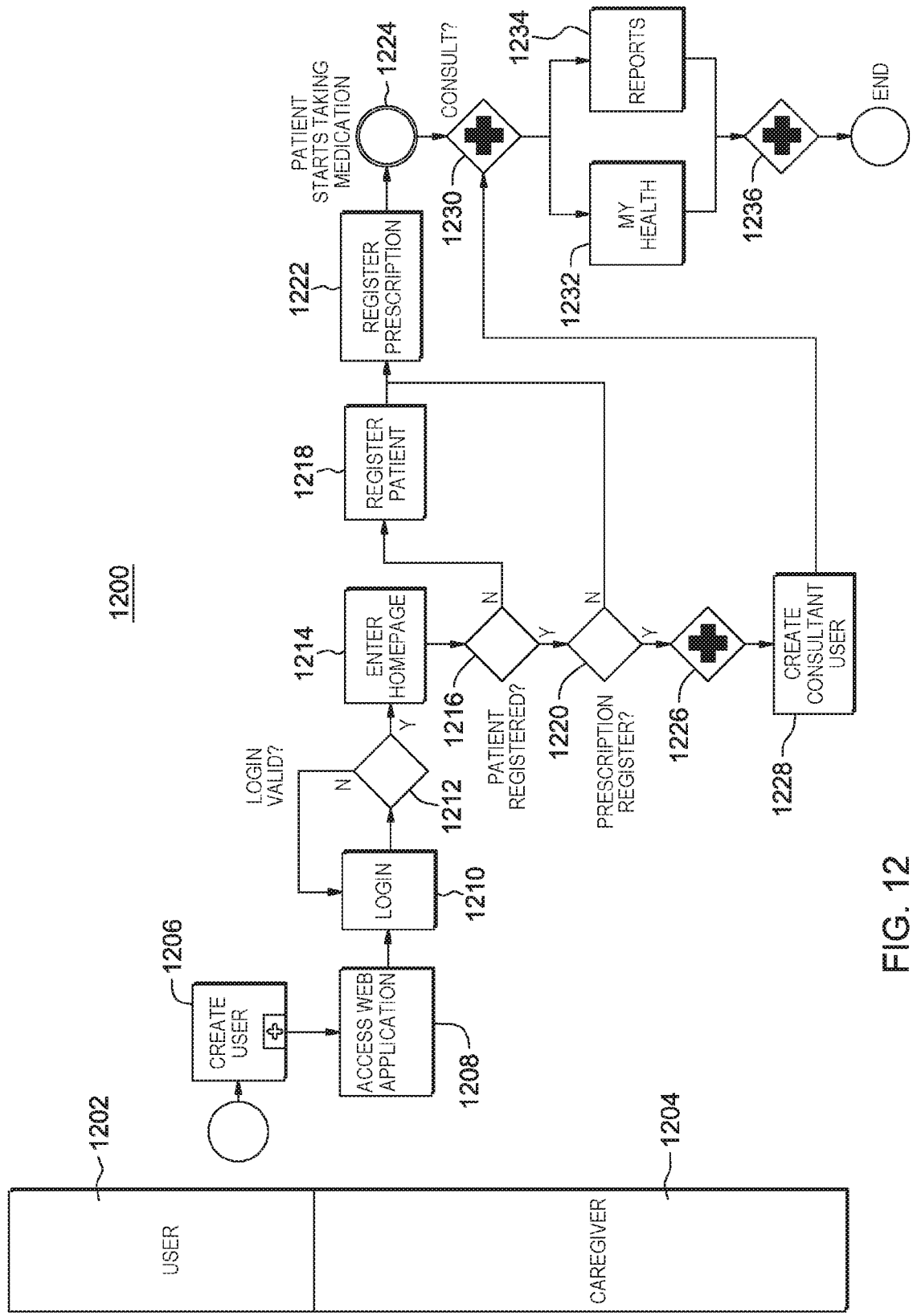
FIG. 12 is a flow diagram illustrating a system flow of the API of FIG. 10 from the perspective of a user and a caregiver in accordance with an aspect of the present disclosure.

With reference now to FIG. 12, a system flow diagram 1200 is illustrated. System flow diagram describes a flow through API 602 from the perspective of a user 1202 and caregiver 1204. At 1206, user 1202 creates a user profile. At 1208, the caregiver 1204 accesses API 602 via web interface 604 or application 606. At 1210, caregiver 1204 attempts to log into API 602, for example, using user interface 1100 (FIG. 11A). At 1212, API 602 determines whether the login was valid. If the login was not valid, API 602 returns caregiver 1204 to 1210 and caregiver 1204 attempts to login again. If the login is valid, API 602 presents caregiver 1204 with a home page at 1214, for example, via web interface 604 or application 606. The homepage may allow the caregiver to register patients, add, remove, or modify prescriptions for patients, or perform other similar administrative functions associated with patients.

At 1216, API 602 determines whether a patient has been registered with the user account. If a patient is not registered, caregiver 1204 may proceed to 1218 to register a patient as described in more detail below with reference to FIG. 14 and may proceed to 1222 to register a prescription for the patient as described in more detail below with reference to FIG. 15. If a patient is registered, caregiver 1204 may proceed to 1220 where API 602 determines whether a prescription has been registered for the patient. If a prescription has not been registered, caregiver 1204 may proceed to 1222 to register a prescription for the patient. Once the prescription has been registered, the patient may be scheduled to start taking the medication according to the registered patient and prescription information at 1224. In some aspects, the patient and prescription information may be synchronized with home medication manager 160 as described above with reference to FIG. 10.

Referring back to 1220, if a prescription has been registered for the patient, caregiver 1204 may proceed to 1226 and may create a consultant user account at 1228. The consultant user account may be used by caregiver 1204 to access the My Health module 708 and reports module 706 associated with the patient. For example, once the consultant account has been created, caregiver 1204 may choose to consult at 1230. In some aspects, once the patient has been scheduled to take the medication at 1224, the caregiver may be given the option to consult at 1230. When consulting, the caregiver 1204 may choose to review the information provided by My Health module 708 or to have reports generated by reports module 706. When caregiver 1204 is finished consulting, caregiver 1204 may proceed to 1236 to end.

Figure 13:
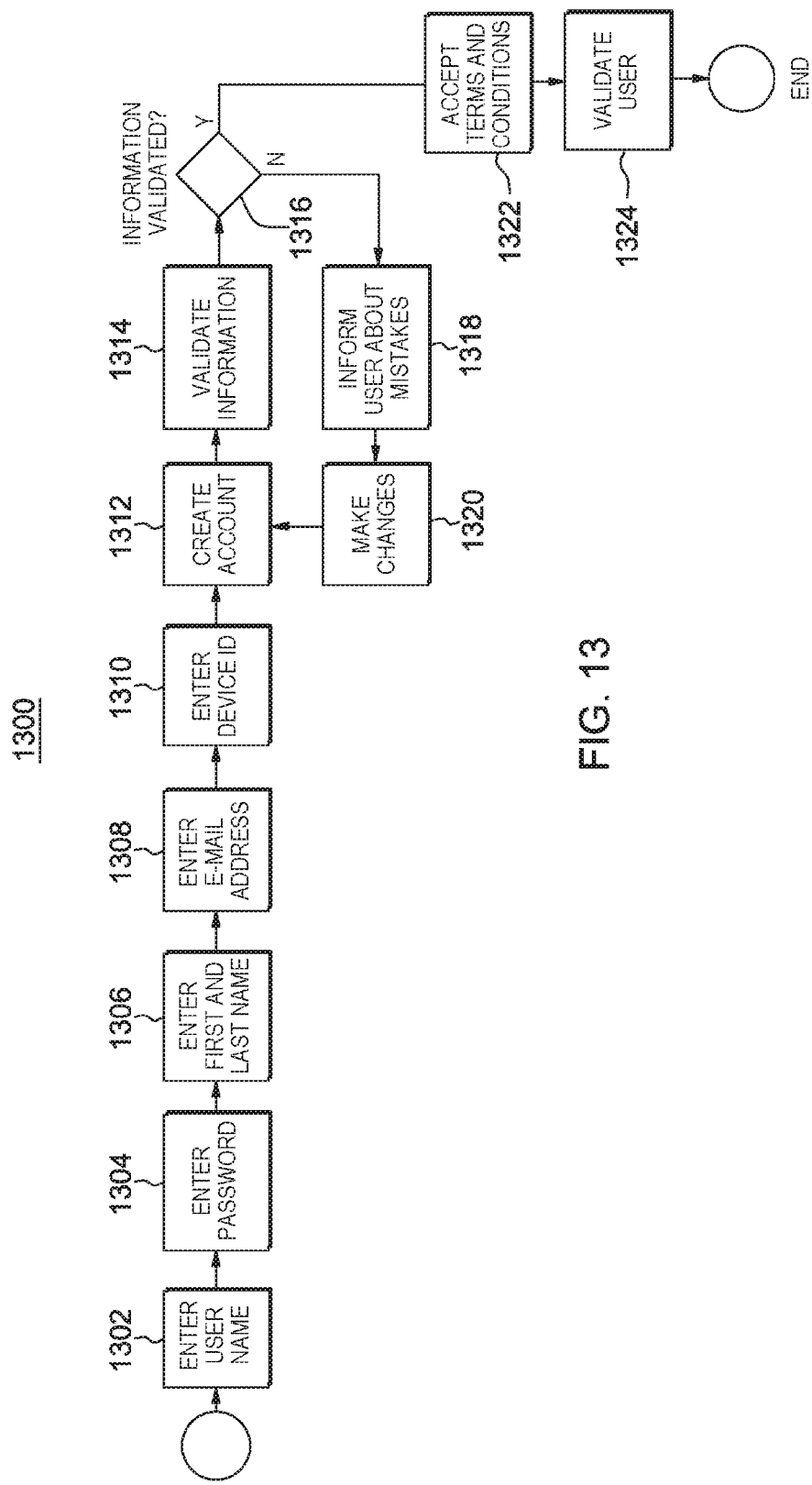
FIG. 13 is a flow diagram illustrating an example flow of the API for the creation of a user account in accordance with an aspect of the present disclosure.

With reference now to FIG. 13, a flow diagram 1300 for creating a user account is illustrated. Flow diagram 1300 illustrates an example flow of a user through API 602 when creating an account, for example, at 1006 of FIG. 10. At 1302, the user may be prompted by API 602 to enter a user name. At 1304, the user may be prompted by API 602 to enter a password. At 1306, the user may be prompted by API 602 to enter a first name and a last name. In some aspects, the user may also be prompted to enter a middle name or initial. At 1308, the user may be prompted by API 602 to enter an e-mail address. At 1310, the user may be prompted by API 602 to enter a device identifier, for example, the identifier associated with a home medication manager 160 to be associated with the user account. In some aspects, each of the above prompts may be presented to the user via a user interface. For example, in some aspects, the user interface may be presented via web interface 604 or application 606. In some aspects, the user may be prompted by API 602 for each of the above items of information at the same time in the same user interface view. In response to the prompts, the user may enter the requested information, for example, in an input field associated with each prompt. In some aspects, the information entered by the user may be stored in memory 124 of computing device 120 or memory 144 of server 140.

At 1312, API 602 may create the user account based on the information provided by the user. At 1314, API 602 may validate the information provided by the user. For example, API 602 may validate the user by transmitting a confirmation message to the user's e-mail address, verifying the user's identity by comparing the entered information to information stored in a database (e.g., a hospital database, doctors office database, etc.), by presenting the user with a prompt including the information and requesting that the user confirm the information, or in another similar manner. At 1316, API 602 determines whether the information has been validated. If the information has not been validated, API 602 may present the user with an indication that the information includes mistakes at 1318 and may provide the user with the opportunity to update the user's information at 1320. Once the user's updated information has been entered, API 602 may create or modify the account at 1312 with the updated information and may validate the updated information at 1314.

One again at 1316, if API 602 determines that the information has been validated, either based on the original information or based on the updated information, API 602 may present the user with a prompt requesting that the user accept terms and conditions of using system 100. Once acceptance of the terms and conditions has been received, API 602 may validate the user for access to system 100 and allow the user to add/remove/modify patients, prescriptions, etc.

Figure 14:
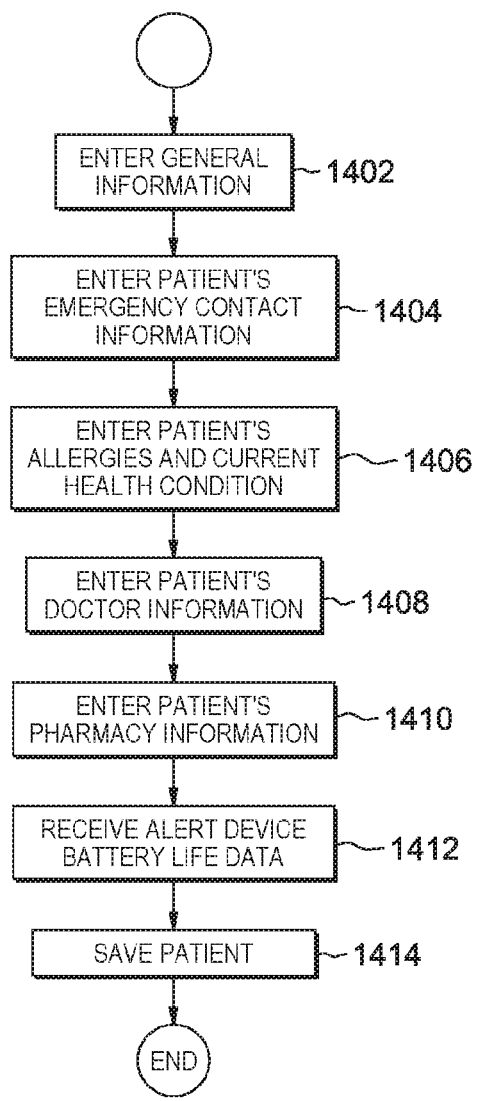
FIG. 14 is a flow diagram illustrating an example flow of the API for the registration of a patient in accordance with an aspect of the present disclosure.

Referring now to FIG. 14, a flow diagram 1400 for registering a patient is illustrated. Flow diagram 1400 illustrates an example flow of a user through API 602 when registering a patient, for example, at 1012 of FIG. 10. At 1402, API 602 may prompt the user to enter general information about the patient including, for example, patient name, address, date of birth, primary physician, or other similar information commonly received by a medical entity from a patient. At 1404, API 602 may prompt the user to enter emergency contact information. For example, the user may be prompted to enter a name, phone number, relation, or other similar information that may be used to contact and validate an emergency contact. At 1406, API 602 may prompt the user to enter information about the patient's allergies and current health conditions. At 1408, API 602 may prompt the user to enter information about the patient's doctors, e.g., the patient's primary care physician, specialists, treating doctors, etc. At 1410, API 602 may prompt the user to enter information about the patient's pharmacy, for example, pharmacy name, location, phone number, etc. At 1412, in some aspects, API 602 may receive or retrieve battery life information for the patient's assigned alert device 180. For example, API 602 may query the patient's assigned alert device 180 for battery life data and may receive the battery life data from the patient's assigned alert device 180. In some aspects, the battery life data may be analyzed to determine a battery life of the patient's assigned alert device 180. The received battery life data or determined battery life may be associated with the patient in API 602. In some aspects, a user may manually review the patient's assigned alert device 180 or battery life data received from the patient's alert device 180 to determine how much battery life is remaining for the patient's assigned alert device 180 and may enter the determined battery life into API 602.

In some aspects, each of the above prompts may be presented to the user via a user interface. For example, in some aspects, the user interface may be presented via web interface 604 or application 606. In some aspects, the user may be prompted by API 602 for each of the above items of information at the same time in the same user interface view. In response to the prompts, the user may enter the requested information, for example, in an input field associated with each prompt. At 1414, API 602 may save the entered patient information in memory 144, for example, via repository interface 612.

Figure 15:
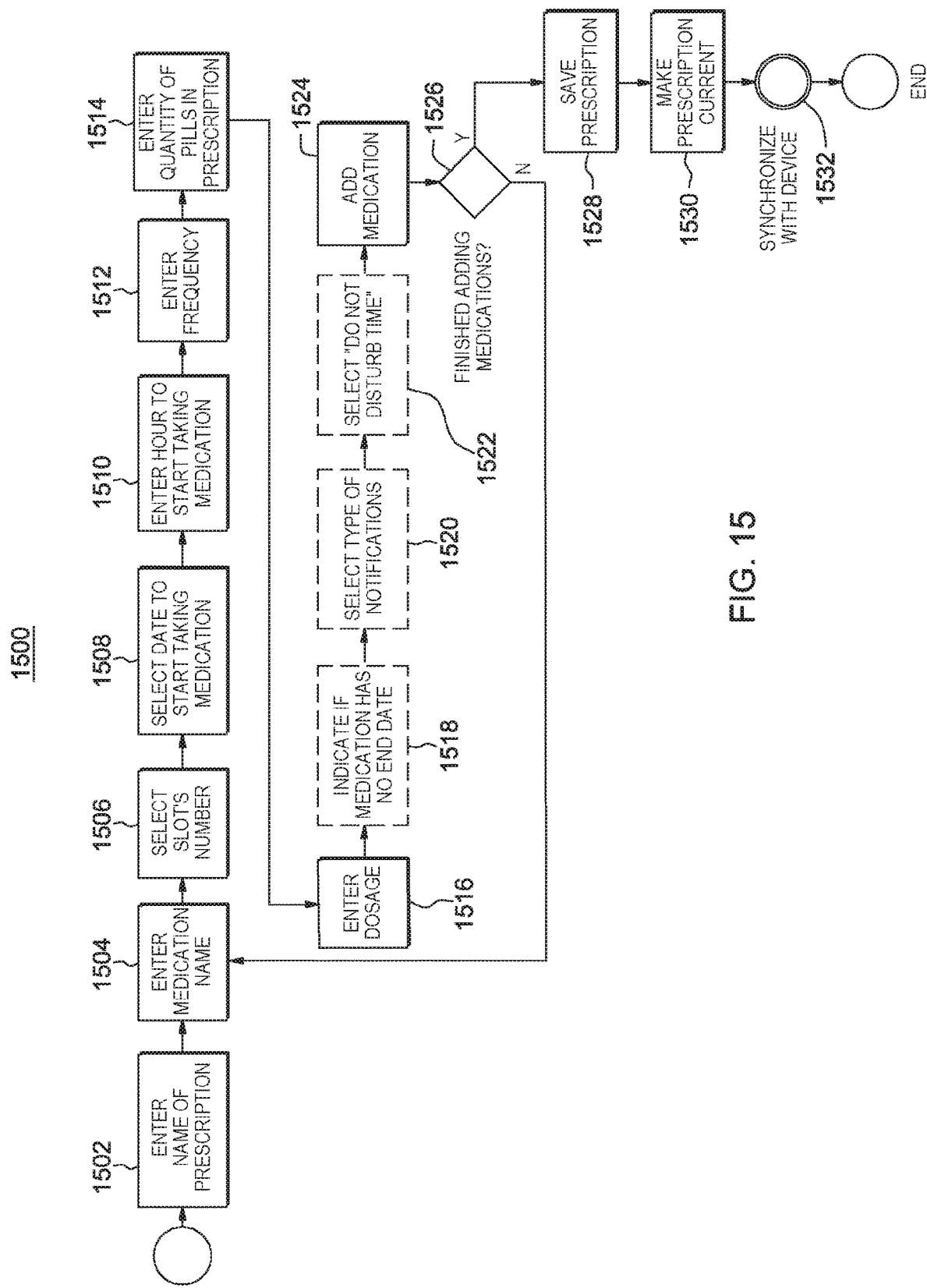
FIG. 15 is a flow diagram illustrating an example flow of the API for the registration of a prescription in accordance with an aspect of the present disclosure.

Referring now to FIG. 15, a flow diagram 1500 for registering a prescription is illustrated. Flow diagram 1500 illustrates an example flow of a user through API 602 when registering a prescription, for example, at 1014 or 1016 of FIG. 10. At 1502, API 602 may prompt the user to enter a name of the prescription to be registered. At 1504, API 602 may prompt the user to enter a name of the medication associated with the prescription. At 1506, API 602 may prompt the user to select a recess number for storage of the prescription container, e.g., one of recesses 208. At 1508, API 602 may prompt the user to select a date for the patient to start taking the medication. At 1510, API 602 may prompt the user to enter a time, e.g., minute, hour, etc., for the patient to start taking the medication. In some aspects, API 602 may present calendar module 804 to the user for selecting a start date and start time. At 1512, API 602 may prompt the user to enter a frequency at which the patient needs to take the medication, e.g., every two hours, four hours, six hours, eight hours, twelve hours, daily, or any other frequency. For example, the frequency may be included on the medication container 210. At 1514, API 602 may prompt the user to enter a quantity of pills included in the prescription. For example, if the medicine container 210 includes thirty pills, the user may enter thirty as the quantity of pills in the prescription. In some aspects, the quantity for the prescription may be determined based on the frequency of the prescription, a duration of the prescription and a dosage of the prescription. At 1516, API 602 may prompt the user to enter a dosage for the prescription. At 1518, in some aspects, API 602 may prompt the user to optionally indicate whether the medication has no end date. At 1520, in some aspects, API 602 may prompt the user to optionally select the type of notifications to be used for the patient for this prescription, e.g., SMS, e-mail, push notifications, visual indications, audio indications, etc. At 1522, in some aspects, API 602 may prompt the user to optionally select do not disturb times. As an example, the user may select a time during which the patient is expected to be sleeping as a do not disturb time. In some aspects, the user may not select any do not disturb times. At 1524, API 602 may add the medication to the prescription. At 1526, API 602 may prompt the user to add additional medications for the prescription. For example, if additional medications need to be added for the prescription, the user may request to add additional medications in response to the prompt and be returned to 1504. If no more medications need to be added, API 602 may save the prescription at 1528. At 1530, API 602 may make the prescription current as described in more detail below with reference to FIG. 16. At 1532, API 602 may synchronize the prescription with home medication manager 160.

Figure 16:
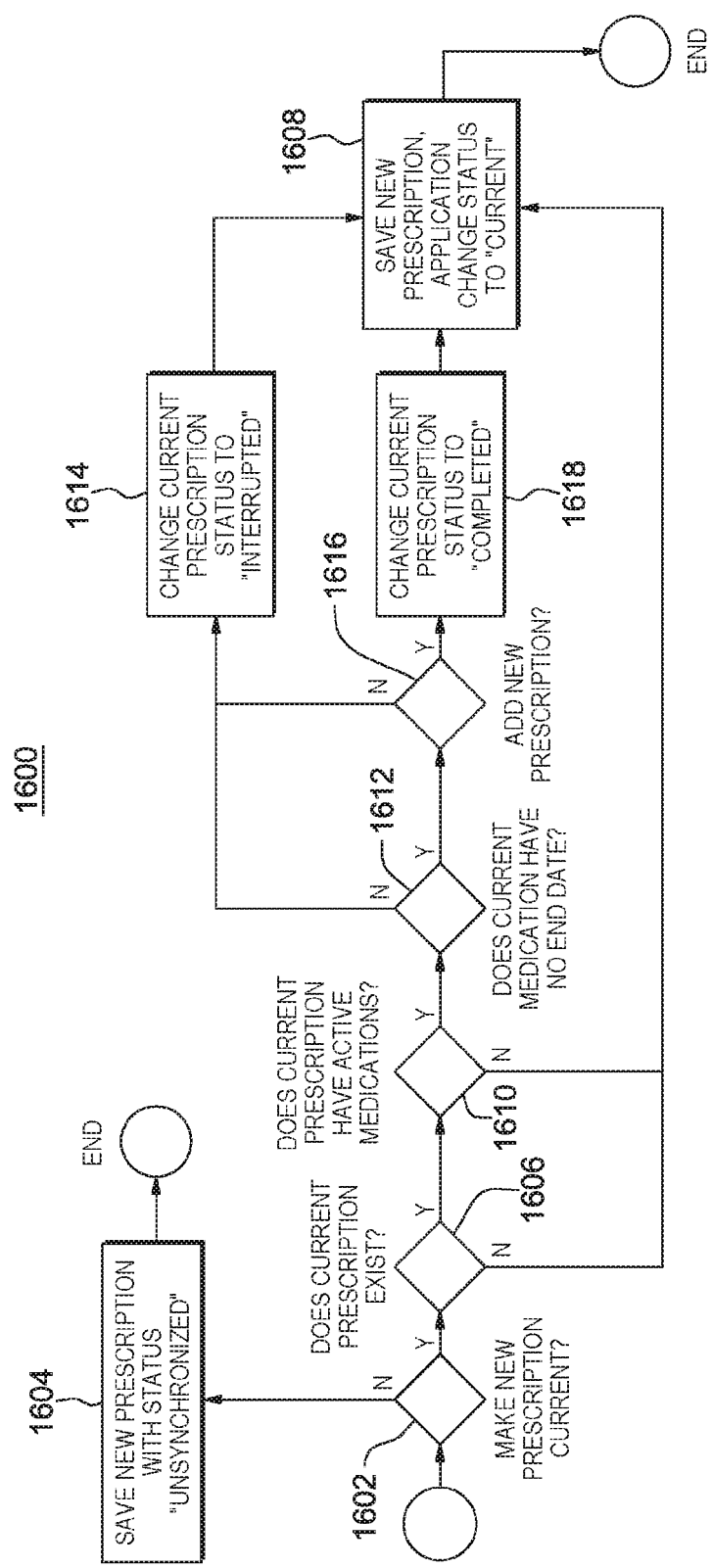
FIG. 16 is a flow diagram illustrating an example flow of the API making a prescription current in accordance with an aspect of the present disclosure.

Referring now to FIG. 16, a flow diagram 1600 for making a new prescription current is illustrated. Flow diagram 1600 illustrates an example flow of API 602 when making a new prescription current, for example, at 1530 of FIG. 15. At 1602, API 602 determines whether to make a new prescription current. For example, if a new prescription has been entered, API 602 may determine that the new prescription may need to be made current. In some aspects, API 602 may make a new prescription current when the start date entered by the user at 1508 (FIG. 15) arrives. In some aspects, for example, API 602 may make the new prescription current upon an expiration of a current medication or prescription that is taken by the patient, e.g., the new prescription includes a medication that is a continuation or replacement for the current medication. In some aspects, for example, API 602 may make the new prescription current after the amount of pills input by the user from a prior prescription have been taken. If API 602 determines that the new prescription should not be made current, API 602 may save the new prescription in memory 144 with a status "unsynchronized" at 1604 for later use and end. In some aspects, the new prescription may be saved as "unsynchronized" and may include an end date for when the prescription should be made current.

If API 602 determines that the new prescription should be made current, API 602 may determine whether a current prescription that corresponds to the new prescription already exists at 1606. For example, API 602 may compare the new prescription to prescriptions already saved by API 602 in memory 144 to determine if a current prescription already exists. If a current prescription does not exist, API 602 may save the new prescription in memory 144 with a status of "Current" at 1608.

If a current prescription already exists, API 602 may determine whether the current prescription has an active medication at 1610. If the current prescription does have an active medication, API 602 may save the new prescription in memory 144 with a status of "Current" at 1608.

If the current prescription has an active medication, API 602 may determine whether the active medication has no end date at 1612. If the active medication has an end date, API may change the current prescription status to "Interrupted" and save the current prescription status in memory 144 at 1614. API 602 may then save the new prescription in memory 144 with a status of "Current" at 1608.

If the active medication has no end date, API 602 may determine whether to add the new prescription at 1616. If API 602 determines not to add the new prescription, API 602 may change the current prescription status to "Interrupted" and save the current prescription status in memory 144 at 1614. API 602 may then save the new prescription in memory 144 with a status of "Current" at 1608.

If API 602 determines to add the new prescription, API 602 may change the current prescription status to "Completed" and save the current prescription status in memory 144 at 1618. API 602 may then save the new prescription in memory 144 with a status of "Current" at 1608. In this manner, API 602 may make a prescription current.

Figure 17:
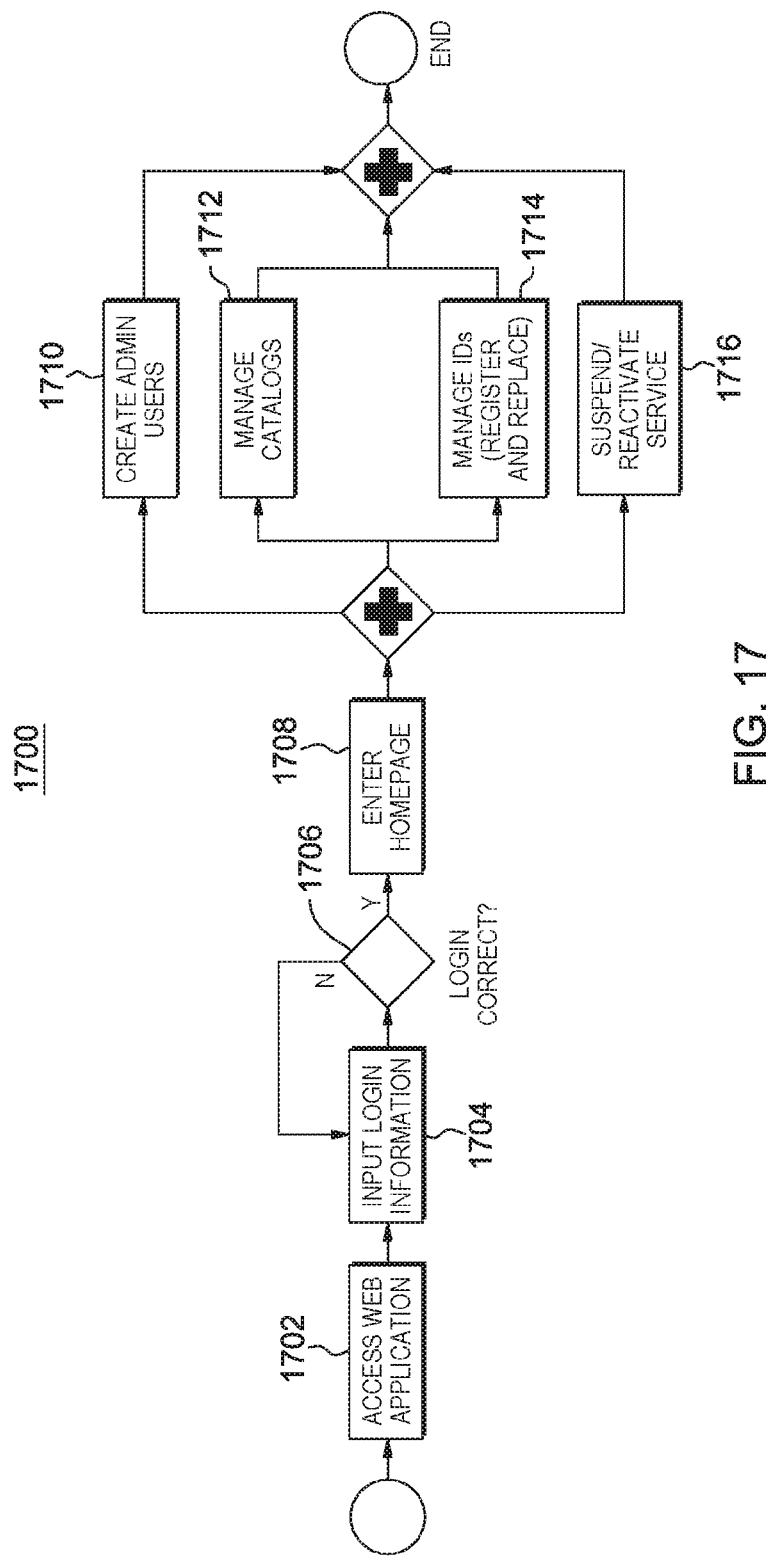
FIG. 17 is a flow diagram illustrating an example flow of the API for administrative users in accordance with an aspect of the present disclosure.

Referring now to FIG. 17, a flow diagram 1700 for administration user functionalities is illustrated. Flow diagram 1700 tracks the flow of an administrative user through API 602. At 1702, an administrative user may access API 602, for example, via web interface 604 or application 606. At 1704, API 602 may prompt the administrative user for login information, for example, username and password, retinal scan, finger print, facial recognition data, or any other form of login information. At 1706, API 602 may determine whether the login information is correct. If the login information is not correct, API 602 may return to 1704 and prompt the administrative user to input the login information again. In some aspects, API 602 may require the administrative user to input additional login information if the login information is not correct a pre-determined number of times.

If the login information is correct, API 602 may present a homepage to the administrative user at 1708. The homepage may be presented as part of a user interface provided, for example, via web interface 604 or application 606. In some aspects, the homepage may provide the administrative user with one or more elements that are activatable to manage the creation of administrative users at 1710, catalogs using catalog module 902 at 1712, identifiers for the registration and replacement of home medication managers 160 using identifier management module 904 at 1714, and the suspension and reactivation of user accounts using service suspending module 906 at 1716.

The computing device 120, server 140, home medication manager 160, alert device 180, and receivers 190 may be any type of known or will be known systems and may include one or more of processors, memory devices, storage devices, input/output devices, internal buses, and/or communications interfaces for communicating with other computer systems in conjunction with communication hardware and software, etc. Portions of the systems also may be implemented on a virtual computer system, colloquially known as a cloud.

Regarding a computer readable storage medium, it may be, for example, a magnetic, optical, electronic, electromagnetic, infrared, or semiconductor system, apparatus, or device, or any suitable combination of the foregoing; however, the computer readable storage medium is not limited to these examples. Additional particular examples of the computer readable storage medium can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an electrical connection having one or more wires, an optical fiber, an optical storage device, or any appropriate combination of the foregoing; however, the computer readable storage medium is also not limited to these examples. Any tangible medium that can contain, or store a program for use by or in connection with an instruction execution system, apparatus, or device could be a computer readable storage medium.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

What is claimed is:

1. A home medication management system, comprising:
a home medication management device of a patient comprising a recess that is configured to store a medication container;
a computing device associated with a user of the home medication management system; and
a remote server that is in communication with the home medication management device and the computing device, the server comprising:
at least one processor comprising hardware;
memory storing an application program interface (API) that is configured to manage the home medication of a patient, the API, when executed by the at least one processor, configured to:
prompt the user via the computing device to register a prescription for a patient registered to an account of the user;
receive from the user, via the computing device, prescription information about a medication included in the prescription, the prescription information comprising:
a name of the medication;
a dosage of the medication;
a frequency at which the patient needs to take the medication; and
a date and time that the patient will start taking the medication;
register the prescription for the patient based on the received prescription information;
transmit the registered prescription to the home medication management device of the patient, the home medication management device configured to:
associate the medication of the registered prescription with the recess of the home medication management device;
provide an indication of the associated recess to the patient for the reception of a medicine container containing the medication;
determine that the medication container containing the medication has been received within the associated recess;
present an alert to the patient at a scheduled time to take the medication based on the prescription information;
provide an indication of the associated recess to the patient, the indication identifying the recess as containing the medication container for the medication that the patient is scheduled to take;
monitor the patient for compliance with the alert by determining whether the medication container containing the medication has been removed from the associated recess; and
transmit compliance data based on the monitoring to the server;
the API further configured to:
receive the compliance data from the home medication management device;
determine, based on the received compliance data, whether the patient has taken the medication as scheduled; and
present the determination to the user via the computing device.

2. The home medication management system of claim 1, wherein the determination of whether the patient has taken the medication as scheduled includes determining whether a pre-determined amount of time has elapsed since the alert was presented to the patient without the patient taking the medication.

3. The home medication management system of claim 2, wherein the determination is presented to the user only if the predetermined amount of time has elapsed.

4. The home medication management system of claim 1, wherein the user is the patient.

5. The home medication management system of claim 1, wherein the user is selected from the group consisting of a doctor of the patient, a caregiver of the patient, an emergency contact of the patient, and a relative of the patient.

6. The home medication management system of claim 1, wherein the presentation of the determination to the user comprises at least one of a text message, an e-mail, and a push notification.

7. The home medication management system of claim 1, wherein the API, when executed by the at least one processor, is configured to present to the user via the user device at least one report comprising at least one of:
medication lists for the patient;
historical data on the patient's compliance with scheduled medications; and
data on emergency notifications.

8. The home medication management system of claim 1, wherein the API is further configured to present to the patient via a computing device associated with the patient at least one of:
clinical history of the patient;
prescription history of the patient;
compliance history of the patient;
current prescriptions registered to the patient in the API; and future prescriptions registered to the patient in the API.

9. The home medication management system of claim 8, wherein the compliance history comprises a percentage of medications that the patient has taken as scheduled in a period of time.

10. The home medication management system of claim 1, wherein, the API is further configured to:
prompt the user via the computing device to set access rights for users associated with the patient; and
receive from the user via the computing device access right settings for users associated with the patient.

11. The home medication management system of claim 1, further comprising an alert device that comprises:
a network interface; and
an output device.

12. The home medication management system of claim 11, wherein the alert device is configured to:
receive an alert from at least one of the computing device, the home medication management device or the server via the network interface, and
present, to the user, through the output device, an alert that it is time to take a medication.

13. The home medication management system of claim 11, wherein the alert device is configured to:
receive an alert from at least one of the computing device, the home medication management device or the server via the network interface, and
present, to the patient, through the output device, an alert that it is time to take a medication.

14. The home medication management system of claim 1, wherein the remote server is not located within the home medication management device.

15. The home medication management system of claim 14, wherein the computing device is not located within the home medication management device.

\* \* \* \* \*